(12) United States Patent
Tsuji et al.

(10) Patent No.: US 6,547,792 B1
(45) Date of Patent: Apr. 15, 2003

(54) BONE FIXING PIN

(75) Inventors: Koichiro Tsuji, Tokyo (JP); Taichi Okutani, Tokyo (JP)

(73) Assignee: Gunze Limited, Kyoto-fu (JP)

( * ) Notice: Subject to any disclaimer, the term of this patent is extended or adjusted under 35 U.S.C. 154(b) by 0 days.

(21) Appl. No.: 09/622,258

(22) PCT Filed: Feb. 10, 1999

(86) PCT No.: PCT/JP99/00585

§ 371 (c)(1),
(2), (4) Date: Aug. 14, 2000

(87) PCT Pub. No.: WO99/40865

PCT Pub. Date: Aug. 19, 1999

(30) Foreign Application Priority Data

Feb. 13, 1998 (JP) .......................... 10-048913

(51) Int. Cl.⁷ .............................. A61B 17/86
(52) U.S. Cl. .......................... 606/72; 606/77
(58) Field of Search .................. 606/59, 72, 60, 606/86, 75–77

(56) References Cited

U.S. PATENT DOCUMENTS

| 4,944,742 A | * | 7/1990 | Clemow et al. | ............... 606/59 |
| 5,112,331 A | * | 5/1992 | Miletich | .................. 606/53 |
| 5,374,270 A | * | 12/1994 | McGuire et al. | ............... 606/86 |
| 5,522,817 A | * | 6/1996 | Sander et al. | .................. 606/72 |
| 5,609,595 A | * | 3/1997 | Pennig | .................. 606/73 |
| 5,827,285 A | * | 10/1998 | Bramlet | .................. 606/60 |
| 5,868,749 A | * | 2/1999 | Reed | .................. 606/76 |
| 5,928,236 A | * | 7/1999 | Augagneur et al. | ........... 606/73 |
| 5,968,047 A | * | 10/1999 | Reed | .................. 606/76 |
| 6,048,343 A | * | 4/2000 | Mathis et al. | .................. 606/72 |
| 6,059,785 A | * | 5/2000 | Schavan et al. | .................. 606/73 |
| 6,197,031 B1 | * | 3/2001 | Barrete et al. | ................. 606/80 |
| 6,210,376 B1 | * | 4/2001 | Grayson | .................... 606/264 |

* cited by examiner

Primary Examiner—Eduardo C. Robert
Assistant Examiner—Michael B. Priddy
(74) Attorney, Agent, or Firm—Browdy and Neimark

(57) ABSTRACT

A bone fixing pin comprising a pin body section (2) consisting of poly-L-lactic acid and a metallic perforating section (3) joined to the pin body section (2) and having a drill (4) at a head thereof, wherein at least the pin body section (2) is, preferably both the pin body section (2) and the perforating section (3) are, formed to have a cylindrical shape having the same diameter through the whole of the length direction thereof. Accordingly, the bone fixing pin can be embedded into (buried into) bone fragments to be fixed easily and smoothly. In addition, loose is never caused to occur after the embedding. The embedded pin body section (2) consisting of poly-L-lactic acid is absorbed in an organism to be eliminated after synostosis.

21 Claims, 5 Drawing Sheets

BONE FIXING PIN

CROSS REFERENCE TO RELATED APPLICATION

The present application is the national stage under 35 U.S.C. 371 of PCT/JP99/00585, filed Feb. 10, 1999.

TECHNICAL FIELD

This invention relates to a bone fixing pin which is for use in fixation in osteosynthese, fixation after osteotomy, fixation of a transplantation bone, arthrodesis, complement, or supporting in an orthopedical and the like areas. The invention relates more concretely to a bone fixing pin which is for use in restoration of fracture portions, such as fixation of fractures of a distal end of humerus, a proximal end of humerus, a distal end of forearm bone, clavicule bone's of digits, and the like, fixation after osteotomy in hallux valgus, rotational acetabular osteotomy, high tibial osteotomy, and the like, fixation of a bone graft (ilium, etc), arthrodesis in polyarthritis rheumatica chronica, arthrodesis in osteoarthritis deformans, and the like, supporting in fracture of a remote end of the radius, and complement or supporting in therapy of osteoporosis.

BACKGROUND TECHNIQUE

When fixation in osteosynthese, fixation after osteotomy, fixation of a transplantation bone, arthrodesis, and so on are carried out in an orthopedical and the like areas, generally employed are methods in which fixation is completed by the use of a metallic implant, such as a screw, a plate, a pin, and a wire, after provisionally fixing a plurality of bone fragments by inserting metallic pin and a metallic wire into the bone fragments to be thereby supported. In these methods, when the metallic pin is used as an implant, the metallic pin must be extracted therefrom by carrying out an extracting operation after bone assimilation. Due to a re-admission to a hospital and a re-operation for extracting the pin, there are problems that QOL (Quality of Life) is reduced and that increase of medical treatment cost is caused. Further, there is a danger of re-fracture, when the pin is extracted therefrom.

Accordingly, a pin which is not required to be extracted after bone assimilation has been used by using such a bio-absorptive polymer as divided gradually in an organism and eliminated after a certain period has passed as a material of a pin. Namely, in order to use this pin, at first, a metallic pin, such as a kirschner steel wire, of which a head is processed to be able to cut a bone is driven into a desirable position, so that bone fragments are provisionally fixed to each other. Next, a perforation is made at the other position by the use of a drill, and a bone fixing pin consisting of the bio-absorptive polymer is pushed into the perforation.

However, in a case of using such a pin, a perforation which dose not attribute to junction of the bone fragments to each other must be made, when the metallic pin for provisional fixation such as kirschner steel wire, is driven thereinto. Further, on a practical use, the metallic pin for provisional fixation is often driven into a position which is the most desirable for restoration and fixation of the bone fragments. This causes a problem that the main bone fixing pin consisting of bio-absorptive polymer is inevitably driven into a next desirable position other than the most desirable position.

Under these circumstances, a proposal is made about a bone fixing pin which is consisting of the bio-absorptive polymer and which can be driven into the most desirable position for the fixation of the bone fragments to each other, since it is not required to fix the bone fragments provisionally to each other by the use of a metallic pin therebefore. Further, in the proposal, a perforation can be made into a bone by this bone fixing pin itself without independently using a drill (See an official gazette of unexamined Japanese Patent Publication Hei 2-63450).

Namely, the bone fixing pin disclosed in the official gazette of unexamined Japanese Patent Publication Hei 2-63450 has a constitution in which a perforating section having a drill is joined to a cylindrical pin body section made from polymeric material. Further, the perforating section having the drill is formed to have a cylindrical shape. On the other hand, the pin body section is formed to have a taper enlarging the diameter thereof toward the direction opposite to that the pin body section is pushed thereinto. Besides, poly-dioxanone is disclosed in the official gazette as a preferable absorptive polymer.

However, in the bone fixing pin disclosed in the above-mentioned official gazette, the pin body section has the taper, so that loose of the pin body section is readily caused to occur within a perforation which is made by the perforating section having the drill. Further, since the pin body section has the taper, strength never become uniform over the whole of the pin body section, in other words, over the whole of a bone-joined portion. In addition, since the bone fixing pin has the taper enlarging the diameter thereof toward the direction opposite to that the pin body section is pushed thereinto, a considerably large strength must be added to make the pin body section be pushed thereinto. A special instrument for the purpose thereof must be prepared. Furthermore, as the poly-dioxanone used as a material for the pin body section has a comparatively small strength, the poly-dioxanone cannot be resistant to a large load. Moreover, the poly-dioxanone is divided comparatively fast in an organism. Accordingly, this bone fixing pin has a problem that applicable portions are restricted to bone's of digits or the like.

The present invention solves the aforesaid problems of the conventional bone fixing pin. It is therefore an object of the present invention to provide a bone fixing pin, which is not required to be extracted therefrom even after bone assimilation, which can readily and smoothly be pushed into the most desirable position for fixation of the bone fragments to each other with the bone fixing pin making a perforation into the bone by itself, in which loose of the bone fixing pin is never caused to occur within the perforation thereby made, and for which applicable portions are increased.

It is yet another object of the present invention to provide use of a bone fixing pin, that is a therapy of osteoporosis.

It is further object of the present invention to provide a bone fixing pin to which roentgenography can be applied.

DISCLOSURE OF THE INVENTION

In order to achieve the above objects, a bone fixing pin of the present invention comprises a pin body section consisting of bio-absorptive high polymer, a perforating section which is joined to said pin body section and which has a drill at a head thereof, and is characterized in that at least said pin body section is formed to have the same thickness through the whole of the length direction thereof.

Namely, according to as aspect of the present invention, there is provided a bone fixing pin comprising: a pin body section consisting of bio-absorptive high polymer; a perforating section which is joined to said pin body section and which has a drill at a head thereof; characterized in that at least said pin body section is formed to have the same thickness through the whole of the length direction thereof.

Preferably, said perforating section is formed to have a cylindrical shape having a drill at a head thereof, and said pin body section is formed to have a cylindrical shape having the same diameter through the whole of the length direction thereof.

Further desirably, substantially whole of said bone fixing pin consisting of both said perforating section except for said drill at a head thereof and said pin body section is formed to have a cylindrical shape having the same diameter through the length direction thereof.

Herein, the bio-absorptive high polymer constituting said pin body section means a high polymeric material that is used as an implant material for operation and that is gradually absorbed in an organism and naturally eliminated after the operation.

Listed hereinunder can be used as the bio-absorptive high polymer.

At first, the following can be listed as synthetic high polymer.

polyester; poly-glycollic acid, poly-lactic acid, poly-L-lactic acid, poly-D-lactic acid, poly-D, L-lactic acid, poly-caprolacton, poly-dioxanone, poly-lacton, poly-(α-malic acid), poly-(β-malic acid), poly-(α, β-malic acid), etc.

polyamino acid; poly-glutamic acid, poly-aspartic acid, etc.

polycarbonate; poly-trimethylene carbonate, etc.

poly-(α-cyanoacrylate); poly-(α-cyanoacrylate), etc.

anhydride; poly-anhydride, etc.

ortho ester; poly-ortho ester, etc.

having nitrogen-phosphorus bond; poly-phosphazen, etc.

Further, the following can be listed as natural high polymer.

polyester; poly-hydroxybutyric acid, poly-hydroxyvaleric acid, etc.

polypeptide; gelatin, collagen, etc.

polyphosphate, polyglycoside; starch, chitin, etc.

The above-listed high polymer or copolymer combining the above-listed high polymer together can be used as the bio-absorptive high polymeric material constituting the pin body section.

Further, composites having a high bio-affinity, such as hydroxyapatite, calcium phosphate, calcium hydrogenphosphate, calcium carbonate, calcium hydrogencarbonate, or the like may be added to said bio-absorptive high polymeric material as an additive. Accordingly, bio-affinity of the bone fixing pin can be improved. Further, hydroxyapatite, calcium phosphate, calcium hydrogenphosphate, calcium carbonate, calcium hydrogencarbonate, or the like is more hard to be transmitted by X-ray, compared with the bio-absorptive high polymer. By adding these, X-ray transmittance of the bio-absorptive high polymer can be reduced. It becomes easy to confirm a position, a condition of disappearance, and the like of the bone fixing pin by roentgenography after operation. Hydroxyapatite and calcium phosphate are preferable as an additive.

Preferably, the following can be listed as the bio-absorptive high polymer.

Namely, the following can be listed as synthetic high polymer.

polyester; poly-glycollic acid, poly-lactic acid, poly-L-lactic acid, poly-D-lactic acid, poly-D, L-lactic acid, poly-caprolacton, poly-dioxanone, poly-lacton, poly-(α-malic acid), poly-(β-malic acid), poly-(α,β-malic acid), etc.

polyamino acid; poly-glutamic acid, poly-aspartic acid, etc.

polycarbonate; poly-trimethylene carbonate, etc.

poly-(α-cyanoacrylate); poly-(α-cyanoacrylate), etc.

anhydride; poly-anhydride, etc.

ortho ester; poly-ortho ester, etc.

having nitrogen phosphorus bond; poly-phosphazen, etc.

Further, the following can be listed as natural high polymer.

polyester; poly-hydroxybutyric acid poly-hydroxyvaleric acid, etc.

polyphosphate;

polyglycoside; chitin, etc.

As a copolymer, a copolymer combining mainly polyester (for example, poly-glycollic acid, poly-lactic acid, poly-L-lactic acid, poly-caprolacton, poly-dioxanone) and subordinately the other, a copolymer including poly-L-lactic acid, a stereocomplex blending poly-L-lactic acid and poly-D-lactic acid, and the like are preferable.

Further, poly-L-lactic acid including hydroxyapatite, poly-L-lactic acid including calcium phosphate, a copolymer including poly-L-lactic acid, a stereocomplex blending poly-L-lactic acid and poly-D-lactic acid, and the like are also preferable.

In particular, poly-L-lactic acid, a copolymer including poly-L-lactic acid, a stereocomplex blending poly-L-lactic acid and poly-D-lactic acid, poly-L-lactic acid including hydroxyapatite are preferable.

Moreover, as a method of joining said pin body section and said perforating section, for example, a calling method, a screwing method, a hooking method, blinding method, and the like can be listed. Among them, calking method is desirable in respect of strength. Further, also in a method other than the calking method, in order to reinforce the joined portion, there is another method in which the joined portion is fixed by pressurizing therearound, after portions to be joined of said pin body section and said perforating section are interfit to each other.

In particular, in a case that poly-L-lactic acid or a copolymer including poly-L-lactic acid is used as a material of said pin body section, since the poly-L-lactic acid, and so on have a certain strength, the portion joined to the perforating section is easily worked. Thus, in the case, the method in which the joined portion is fixed by pressurizing therearound after portions to be joined of said pin body section and said perforating section are interfit to each other can be readily carried out.

By employing these methods of joining, it is not necessary to use an adhesive for joining the pin body section and the perforating section to each other. Accordingly, it is not dangerous that components of the adhesive remain in an organism, so that the bone fixing pin of the present invention can be safely used.

The best mode for the putting the invention into practice:

In order to describe the present invention more in detail, the description will be made in accordance with the drawings.

Figure 1:
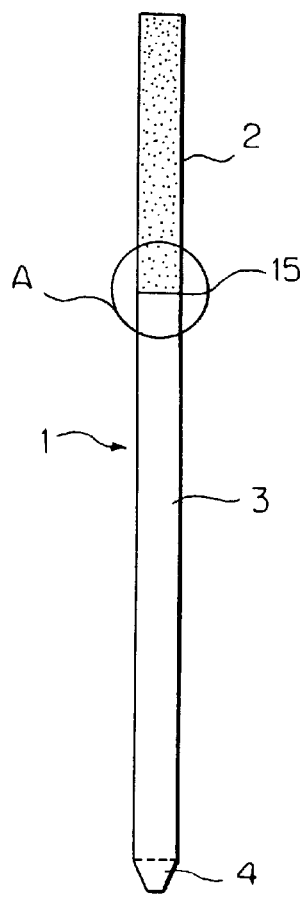
FIG. 1 is a view for showing the whole constitution of a bone fixing pin according to a preferred embodiment of the present invention.
Figure 2:
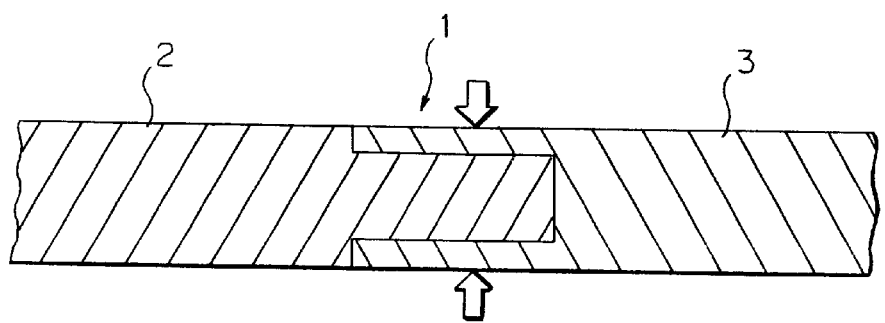
FIG. 2 is a cross sectional view for showing an enlarged portion A of the bone fixing pin illustrated in FIG. 1.
Figure 9:
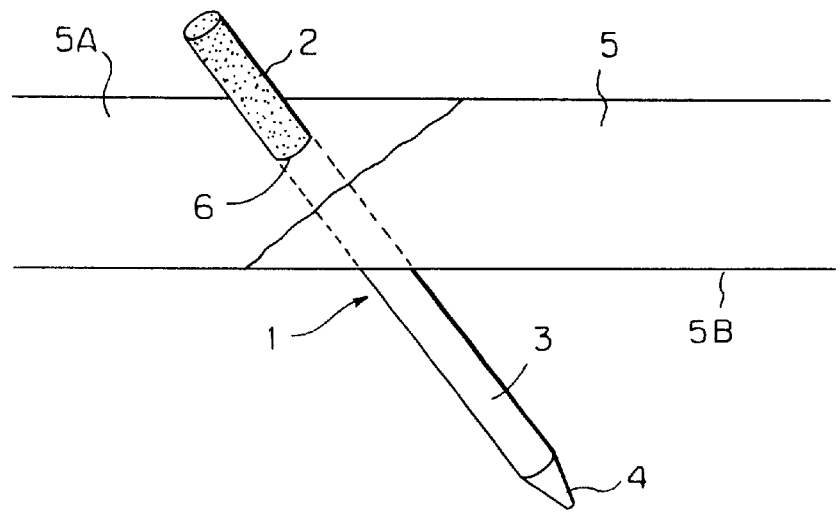
FIG. 9 is a view for explaining the method of using the bone fixing pin illustrated in FIG. 1 and is also a view showing a condition in which a part of the pin body section is buried into the perforation.
Figure 10:
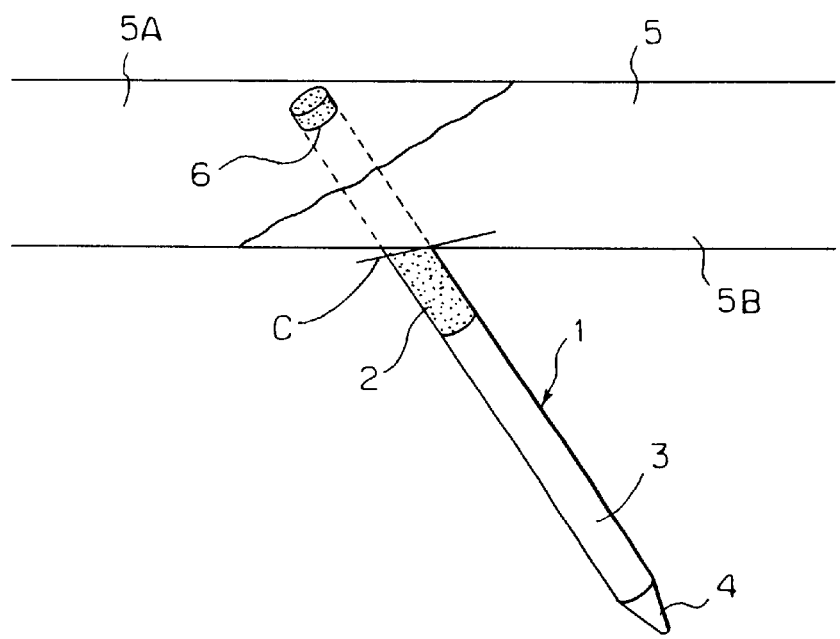
FIG. 10 is a view for explaining the method of using the bone fixing pin illustrated in FIG. 1, and is also a view showing a condition in which substantially whole of the pin body section is completely buried into the perforation.

At first, referring to FIGS. 1, 2, 9 and 10, description is made about a bone fixing pin according to a first embodiment of the present invention. FIG. 1 is a view for showing the whole constitution of a bone fixing pin according to an embodiment of the present invention while FIG. 2 is an enlarged cross-sectional view for showing a portion A in FIG. 1. FIGS. 9 and 10 are views for explaining the method of using the bone fixing pin according to an embodiment of the present invention.

As illustrated in FIG. 1, a bone fixing pin 1 according to an embodiment of the present invention comprises a pin body section 2 and a perforating section 3.

The pin body section 2 is made from poly-L-lactic acid which is a bio-absorptive material and of which strength is comparatively high. Further, the pin body section 2 is formed to have a cylindrical shape having the same diameter through the whole of the length direction thereof. Herein, the diameter and the total length of the cylindrical pin body section 2 may be appropriately selected, dependent on a portion to which the bone fixing pin 1 of the present invention is applied. For example, when small size bone fragments, such as facial inferior floor, bone's of digits, a genual bone, or the like are to be fixed, it is preferable that the cylindrical pin body section 2 has a diameter of 0.6 through 2.0 mm and a total length of 10 through 50 mm. When medium size bone fragments of a brachial portion, an antebrachial portion, an ankle region, ilium for implantation, or the like are to be fixed, it is preferable that the cylindrical pin body section 2 has a diameter of 1.0 through 4.0 mm and a total length of 10 through 100 mm. When large size bone fragments of shoulder bones, clavicle, femur, tibia, fibula, or the like are to be fixed, it is preferable that the cylindrical pin body section 2 has a diameter of 2.0 through 20 mm and a total length of 10 through 500 mm.

Besides, since the cylindrical pin body section 2 is made from poly-L-lactic acid which is a bio-absorptive high polymeric material as described above, the bone fixing pin 1 is more flexible than that having a metallic pin body section. Further, the bone fixing pin 1 would lose the strength thereof gradually in an organism, after having fixed the bone once. The bone fixing pin 1 can therefore be applied to children of which bones are growing.

The perforating section 3 is made of a metal and has a drill portion 4 in a head side thereof. Further, the perforating section 3 is made to have a cylindrical shape including a total length of 150 mm and the same diameter as that of the pin body section 2 except for the drill portion 4. Besides, the diameter of the perforating section 3, similarly to the diameter of the pin body section 2, may be appropriately selected within a range between 0.6 mm and 20 mm, dependent on a portion to which the bone fixing pin 1 is applied. Thus, this embodiment, the diameter of the perforating section 3 through the length direction thereof except for the drill portion 4 is determined to be the same as that of the pin body section 2. Accordingly, as will later be described, once the perforating section 3 has been joined to the pin body section 2, whole of the bone fixing pin 1 except for the drill portion 4 is constituted to have a cylindrical shape having the same diameter through the length direction thereof.

The perforating section 3 is to be joined to the pin body section 2. In this embodiment, as a method of joining, what is called, press-calking method is employed. In the press-calking method, as illustrated in FIG. 2, a convex portion formed in one end of the pin body section 2 is interfit into a recessed portion formed at the end of the opposite side of the perforating section 3 to that of the drill portion 4, and the interfit portion is then calked by pressing from the both sides thereof.

Figure 3:
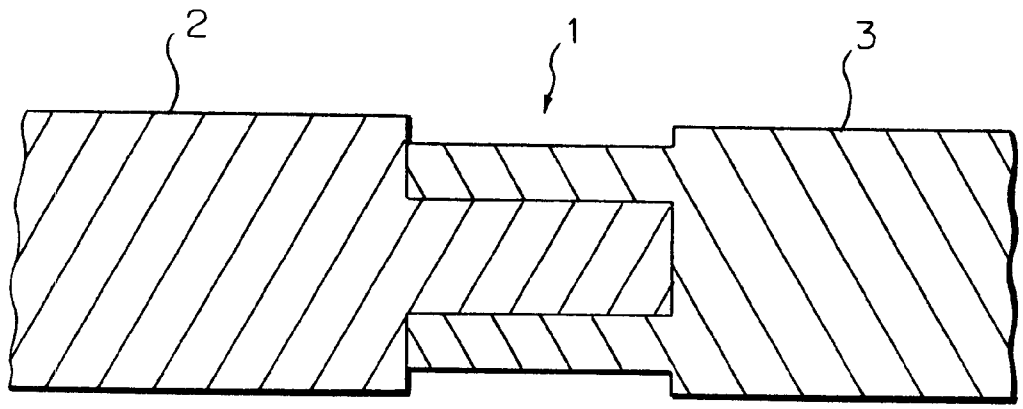
FIG. 3 is a cross sectional view similar to FIG. 2 for showing the portion A of a bone fixing pin according to another embodiment of the present invention.

Besides, dependent on extent to which the interfit portion is thus pressured from the both sides, a structure in which a stage is defined in the joined portion by such a chalking may be alternatively employed, as illustrated in FIG. 3.

Figure 4:
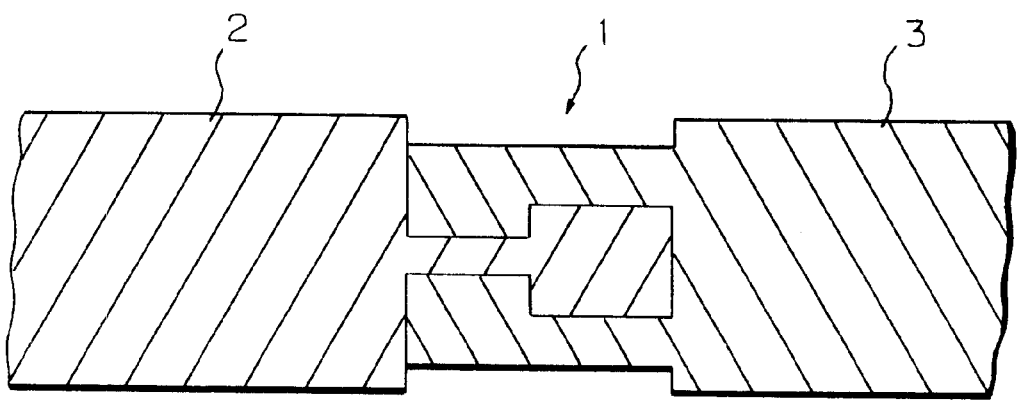
FIG. 4 is a cross sectional view similar to FIG. 2 for showing the portion A of a bone fixing pin according to still another embodiment of the present invention.

Further, a shape of the joined portion is not restricted to those mentioned above. For example, as illustrated in FIG. 4, an alternative structure may be considered. In the alternative structure, the convex portion formed in one end of the pin body section 2 may be formed to have a two-stage structure consisting of a large diameter portion in the head side thereof and a small diameter portion in the root side thereof. With the structure, after the calking, a metal of the perforating section 3 is passed around the small diameter portion to improve the joining strength.

As methods for joining the pin body section 2 with the perforating section 3, the followings can further be considered.

Figure 5:
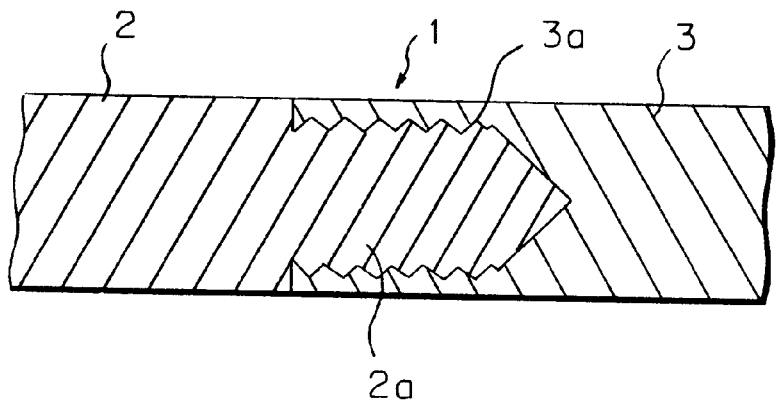
FIG. 5 is a view for explaining a screwing method as a method of joining the pin body section and the perforating section.
Figure 6:
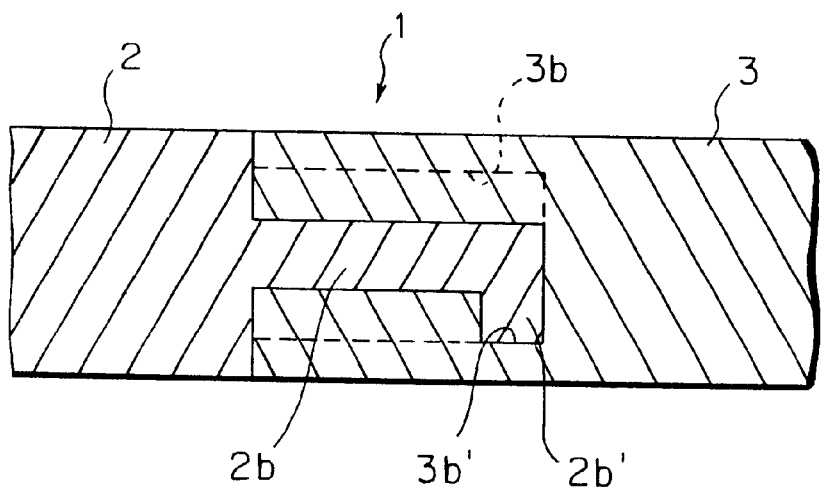
FIG. 6 is a view for explaining a hooking method as a method of joining the pin body section and the perforating section.
Figure 7:
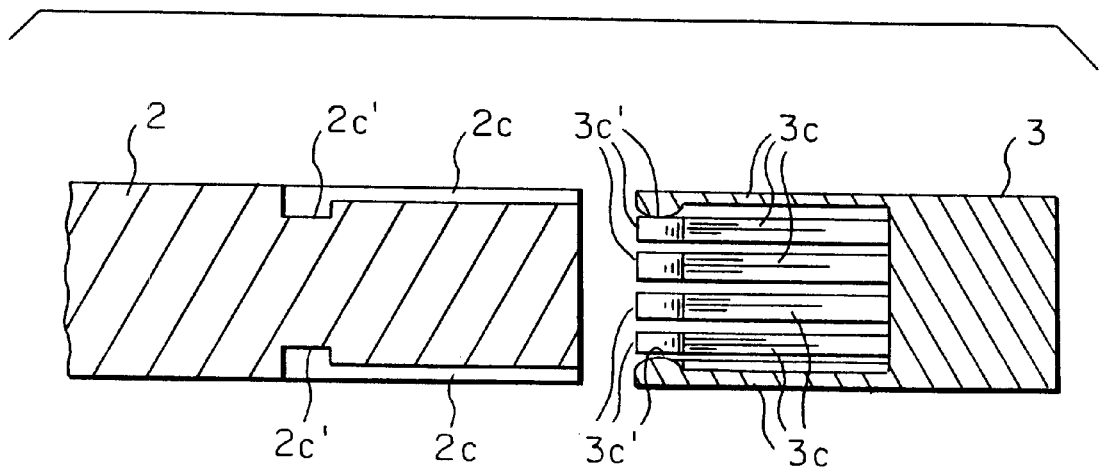
FIG. 7 is a view for explaining a blinding method as a method of joining the pin body section and the perforating section, and is also a cross sectional view showing a condition before the joining.
Figure 8:
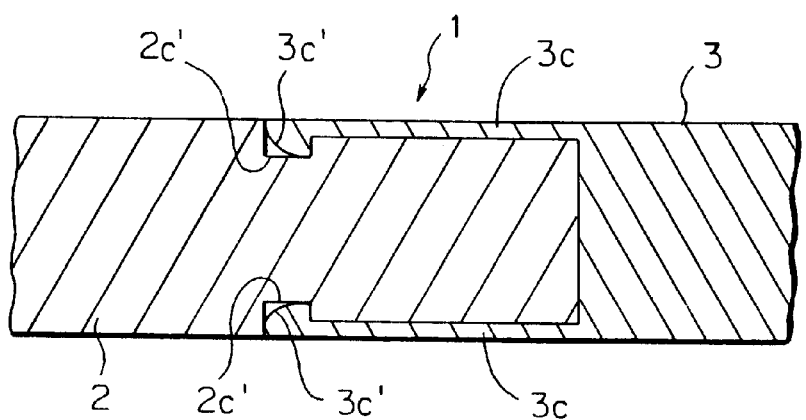
FIG. 8 is a view for explaining a blinding method as a method of joining the pin body section and the perforating section, and is also a cross sectional view showing a condition in which the pin body section and the perforating section have been joined to each other.

In FIG. 5, illustrated in a screwing method, in which a female screw 3a is carved in the one side while a bolt 2a is formed in the other side, and in which the bolt 2a is tightened with the female screw 3a. In FIG. 6, illustrated is a hooking method, in which an inserting portion 2b having a protrusion 2b in perpendicular to the head thereof is formed in the one side. On the other hand, an insertable hole 3b into which the inserting portion 2b is inserted is formed in the other side. Further, a recessed portion 3b, in which the protrusion 2b is inserted to be hooked therein, is formed in the inner part of the insertable hole 3b. Accordingly, by inserting the inserting portion 2b into the insertable hole 3b and twisting the inserting portion 2b therein, the protrusion 2b is hooked in the recessed portion 3b. In FIGS. 7 and 8, illustrated is a bamboo blind method, in which, at the end portion of the one side, a plurality of protruding pieces 3c, 3c are formed in the axial direction thereof with being arranged in a bamboo blind fashion. In addition, protrusions 3c, 3c each of which is protruding to the inside are formed at the heads of these protruding pieces 3c, 3c, respectively. On the other hand, a recessed portion 2c in which the protruding pieces 3c and the protrusions 3c are inserted is formed on the outer circumferential surface of the other side. In this case, the protruding pieces 3c are slided into the recessed portion 2c, and the protrusions 3c are then hooked into an one-stage deeper portion 2c of the recessed portion 2c.

Next, also referring to FIGS. 9 and 10, description is made as regards a method of suing the bone fixing pin 1 according to this embodiment.

FIGS. 9 and 10 are views for explaining the method of using the bone fixing pin 1. FIG. 9 shows a condition in which the bone fixing pin 1 has perforated osseous tissue and a part of the pin body section 2 is buried into a perforation. FIG. 10 further shows a condition in which whole of the pin body section 2 is completely buried into the perforation. Besides, in the figures, 5 shows a bone, 5A and 5B show fractured both bone fragments in a bone 5, and 6 shows a perforation perforated through the both bone fragments 5A and 5B by the drill portion 4.

In the interim, in order to fix bone fragments to each other by the bone fixing pin 1, upon adjusting the bone fragments 5A and 5B as they used to be, at first, a perforation is made in the best position for fixing the bone fragments 5A to 5B by the use of the drill portion 4. With the perforation being made, the perforating portion 3 is buried into a perforation 6 digged by the drill portion 4 through the both bone fragments 5A and 5B, as illustrated in FIG. 9. Further, as illustrated in the figure, when the perforating portion 3 has penetrated from the inward of the perforation 6 down to the opposite side of the bone 5 (In the figure, the lower side of the bone fragment 5B), the perforating portion 3 is gripped by an unillustrated appropriate instrument, such as a hammer having a chuck, or the like so as to be pulled out of the opposite side. Alternatively, the perforation portion 3 is pushed from the upper side of the pin body section 2 by a pinpusher and so on, when the perforating portion 3 has thus penetrated. Accordingly, a condition that a part of the pin body section 2 is exposed from the opposite side of the bone 5 (In the figure, the lower side of the bone fragment 5B) has been achieved, as illustrated in FIG. 10. Thus, according to the bone fixing pin 1 of this embodiment, the perforation 6 in which the pin body section 2 is buried can be made by the use of the drill portion 4 integrated with the perforating portion 3. From the first, the bone fixing pin 1 can be inserted into the best position for fixing bone. Furthermore, according to the bone fixing pin 1 of this embodiment, substantially whole of the bone fixing pin 1 including both the perforating section 3 and the pin body section 2 except for the drill portion 4 is formed to have a cylindrical shape having the same diameter through the length direction thereof. The bone fixing pin 1 can therefore be pushed into (buried into) such the best position for fixing bones readily and smoothly, different from a conventional bone fixing pin, and the like, of which a pin body section is provided with a taper.

Besides, when the perforating portion 3 is gripped to be pulled out, it is sometimes caused to occur that a considerable part of the pin body section 2 is exposed from the opposite side of the bone 5 (In the figure, the lower side of the bone fragment 5B) due to the over pull of the perforating portion 3. Consequently, a length of the remaining part of the pin body section 2 within the bone 5 is not enough to fix the bone fragments 5A and 5B. In such a case, alternatively, the perforating portion 3 may be pushed from the opposite side of the bone 5 (In the figure, the lower side of the bone fragment 5B) to be returned into the perforation 6. In this case, according to the bone fixing pin 1 of this embodiment, since substantially whole of the bone fixing pin 1 including both the perforating section 3 and the pin body section 2 except for the drill portion 4 is formed to have a cylindrical shape having the same diameter through the length direction thereof, a length of a buried part of the pin body section 2 (a position of the pin body section 2 in depth) within the bone 5 can readily be adjusted.

Thereafter, the pin body section 2 is cut at the position projecting from the perforation 6 by the use of an unillustrated appropriate instrument, such as a cutting nipper, a scalpel, or the like, as illustrated in FIG. 10. Besides, C in the figure shows the cutting portion. Accordingly, only the pin body section 2 remains buried within the bone 5, so that the pin body section 2 fixes the bone fragments 5A and 5B. According to the bone fixing pin 1 of this embodiment, at least the pin body section 2 is formed to have a cylindrical shape having the same diameter through the length direction thereof. Loose of the pin body section 2 is never caused to occur within the perforation 6, different from a conventional bone fixing pin, and the like, of which a pin body section is provided with a taper. Further, since strength of the pin body section 2 is uniform over the whole of the pin body section 2, a joined portion of the bone can be fixed to be well-balanced at the uniform strength.

Thereafter, the pin body section 2 is made from poly-L-lactic acid that is the bio-absorptive high polymeric material, the pin body section 2 is gradually absorbed in an organism and naturally eliminated. Therefore, it is not necessary to extract the pin body section 2 from the buried portion by carrying out an extracting operation after bone assimilation. Consequently, it is not caused to occur that QOL is reduced and that medical treatment cost is increased, due to a re-admission to a hospital and a re-operation for extracting the pin body section 2. Further, there is no danger of re-fracture, when the pin is extracted therefrom.

Besides, strength of poly-L-lactic acid used as a material of the pin body section 2 in the bone fixing pin 1 according to this embodiment is larger than that of poly-dioxanone used as a material of a pin body section in the conventional example. As a result, the poly-L-lactic acid used as the material of the pin-body section 2 can be resistant to a comparatively large load. Accordingly, the bone fixing pin 1 can be applied to various portions.

As described above, although the present invention is described in conjunction with the specific embodiment thereof, the present invention is not restricted to the embodiment mentioned above. The present invention can be applied to various other embodiments within the scope described in the claims.

For example, in the above-mentioned embodiment, description was made as regards an example in which substantially whole of the bone fixing pin including both the perforating section and the pin body section except for the drill portion is formed to have a cylindrical shape having the same diameter through the length direction thereof. However, it is enough that at least the pin body section is formed to have the same thickness through the length direction thereof. With the structure thus mentioned, the bone fixing pin can be pushed into (buried into) bones readily and smoothly, compared with a conventional bone fixing pin of which a pin body section is provided with a taper. In addition, lose of the bone fixing pin is never caused to occur even after the bone fixing pin has been buried into the bones.

Therefore, any portions other than the pin body section (the perforating section or a joined portion between the pin body section and the perforating section as well as the drill portion, of course) are not required to have the same diameter, and the like as the pin body section. Further, whole of the bone fixing pin including the pin body section is not required to have a cylindrical shape. For example, another shape having an elliptical or a rectangular cross section, etc.. may be alternative. However, the cylindrical shape (having the circular cross section) is preferable on a practical use. Possibility of industrial use The present invention has a constitution thus mentioned above, that is a bone fixing pin, in which the pin body section buried into a bone is consisting of a the bio-absorptive high polymer, and in which the pin body section can be inserted into the best position for fixing the bone fragments to each other at the same time when the bone fixing pin penetrates the bone. By forming whole of the pin body section to have the same thickness through the length direction thereof, it has become possible that the whole of the pin body section is completely fitted into a perforation made by a drill. Therefore, loose of the pin body section is never caused to occur within the perforation. In addition, since strength of the pin body section is uniform over the whole of the pin body section, a joined portion of the bone fragments to each other can be fixed to be well-balanced at the uniform strength. Particularly, poly-L-lactic acid has a large strength. Therefore, strength of the pin body section is further improved, in a case that the bio-absorptive high polymer is poly-L-lactic acid. Further, the bone fixing pin can smoothly be pushed into the perforation. Any specific instrument is not required for pushing the bone fixing pin into the perforation. In order to enable the bone fixing pin to be used for fixing a large size, a medium size, and a small size bones, it is possible that the bone fixing pin having a size suitable for each of them is provided. Moreover, the pin body section is made from a bio-absorptive material, it is not necessary to carry out an extracting operation after bone assimilation.

In the interim, now pharmacotherapy of the like are carried out as a therapy of osteoporosis. It is also useful to use the bone fixing of the present invention for the purpose of reinforcing the bone of the osteoporosis. Namely, osteoporosis is defined as, for example "A condition in which bone mass is decreased to cause a large danger of fragility fracture", and employed is a therapy for restoring the bone mass in which bone resorption is controlled by estrogen, calcium, calcitonin, activated vitamin D, and the like, and in which osteogenesis is promoted by parathyroid hormone, vitamin $K_2$, androgen, and the like. By burying the bone fixing pin of the present invention into a bone in which bone mass is decreased and bone density becomes small for use in supporting or complement of the bone, it is possible to wait the restoration of bone mass by the pharmacotherapy, or the like, with a danger of fracture being avoided. Besides, the pin body section may be consisting mainly of bio-absorptive high polymer and hydroxyapatite, calcium phosphate, calcium hydrogenphosphate, calcium carbonate, calcium hydrogencarbonate, or the like may be added to the bio-absorptive high polymer as an additive. Accordingly, bio-affinity of the bone fixing pin can be improved. In addition, it becomes easy to confirm a position, and the like of the bone fixing pin by roentgenography after the burying.

What is claimed is:

1. A bone fixing pin comprising:
   a pin body section composed of a bio-absorptive high molecular weight polymer; and
   a perforating section which has a drill at a head thereof, wherein:
      each of said sections has a joining portion at which said pin body section is joined to said perforating section; and
   when said sections are joined together, said fixing pin is thinner at the joining portions than at other portions of said pin body section and said perforating section, and a recessed portion is formed at said joining portions.

2. The bone fixing pin as claimed in claim 1, wherein said polymer is poly-L-lactic acid or a copolymer including poly-L-lactic acid.

3. The bone fixing pin as claimed in claim 1, wherein said pin body section contains an additive composed of at least one of hydroxyapatite, calcium phosphate, calcium hydrogenphosphate, calcium carbonate, and calcium hydrogencarbonate.

4. The bone fixing pin as claimed in claim 1, wherein:
   said pin has a length direction;
   said joining portions are constituted by an insertion portion at an end of one of said sections and a wall surrounding a hollow region at an end of the other one of said sections, said insertion portion being inserted into said hollow region in order to join said pinbody section to said perforating section; and
   said sections are joined together by at least one of:
      pressing said wall against said insertion portion;
      providing said wall with a recessed portion that extends transversely to the length direction and providing said insertion portion with a protrusion that extends transversely to the axial dimension and is fitted into said recessed portion; and
      providing said insertion portion with a recessed portion that extends transversely to the length direction and providing said wall with a protrusion that extends transversely to the length direction and is fitted into said recessed portion.

5. A bone fixing pin having a length direction and comprising:
   a pin body section composed of a bio-absorptive high molecular weight polymer; and
   a perforating section which has a drill at a head thereof, wherein;
   one of said sections has an end provided with an insertion portion and the other of said sections has an end provided with a wall surrounding a hollow region, said insertion portion being inserted into said hollow region in order to join said pin body section to said perforating section; and
   said sections are joined together by at least one of:
      pressing said wall against said insertion portion in a direction transverse to the length direction;
      providing said wall with an end surface that is transverse to the length direction and that bears against a surface of the other one of said sections when said sections are joined together, and providing said hollow region with an undercut portion that is spaced from the end surface of said wall and extends transversely to the length direction and providing said insertion portion with a protrusion that is spaced from the end surface of said wall and extends transversely to the length direction and is fitted into said recessed portion; and providing said insertion portion with a recessed portion that extends transversely to the length direction and providing said wall with a protrusion that extends transversely to the length direction and is fitted into said recessed portion.

6. The bone fixing pin as claimed in claim 5, wherein at least said pin body section has the same thickness through the length direction thereof.

7. The bone fixing pin as claimed in claim 5, wherein substantially all of said bone fixing pin has the same thickness through the length direction thereof.

8. The bone fixing pin as claimed in claim 5, wherein said perforating section has a cylindrical shape and said pin body section has a cylindrical shape having the same diameter through the whole of the length direction thereof.

9. The bone fixing pin as claimed in claim 8, wherein substantially the entirety of said bone fixing pin has the same diameter through the length direction thereof.

10. The bone fixing pin as claimed in claim 5, wherein said polymer is poly-L-lactic acid of a copolymer including poly-L-lactic acid.

11. The bone fixing pin as claimed in claim 5, wherein said pin body section contains an additive composed of at least one of hydroxyapatite, calcium phosphate, calcium hydrogenphosphate, calcium carbonate, and calcium hydrogencarbonate.

12. The bone fixing pin as claimed in claim 5, wherein said pin has the same thickness in the area of said insertion portion and said wall as the remainder of said bone fixing pin.

13. The bone fixing pin as claim in claim 5, wherein each section of said bone fixing pin is made of a material that is observable by X-rays.

14. The bone fixing pin as claimed in claim 13, wherein said pin body section contains an additive composed of at least one of hydroxyapatite, calcium phosphate, calcium hydrogenphosphate, calcium carbonate, and calcium hydrogencarbonate.

15. A bone fixing pin for use in osteoporosis treatment, said bone fixing pin having a length direction and comprising:

a pin body section composed of a bio-absorptive high molecular weight polymer; and a perforating section which has a drill at a head thereof, wherein:

said bone fixing pin is used to support or complement a bone in osteoporosis treatment;

one of said sections has an end provided with an insertion portion and the other of said sections has an end provided with a wall surrounding a hollow region, said insertion portion being inserted into said hollow region in order to join said pin body section to said perforating section; and said sections are joined together by at least one of:

pressing said wall against said insertion portion in a direction transverse to the length direction;

providing said wall with an end surface that is transverse to the length direction and that bears against a surface of the other one of said sections when said sections are joined together, and providing said hollow region with an undercut portion that is spaced from the end surface of said wall and extends transversely to the length direction and providing said insertion portion with a protrusion that is spaced from the end surface of said wall and extends transversely to the length direction and is fitted into said recessed portion; and providing said insertion portion with a recessed portion that extends transversely to the length direction and providing said wall with a protrusion that extends transversely to the length direction and is fitted into said recessed portion.

16. The bone fixing pin as claimed in claim 15, wherein at least said pin body section has the same thickness through the length direction thereof.

17. The bone fixing pin as claimed in claim 15, wherein substantially all of said bone fixing pin has the same thickness through the length direction thereof.

18. The bone fixing pin as claimed in claim 15, wherein said perforating section has a cylindrical shape and said pin body section has a cylindrical shape having the same diameter through the whole of the length direction thereof.

19. The bone fixing pin as claimed in claim 18, wherein substantially the entirety of said bond fixing pin has the same diameter through the length direction thereof.

20. The bone fixing pin as claimed in claim 15, wherein said polymer is poly-L-lactic acid or a copolymer including poly-L-lactic acid.

21. The bone fixing pin as claimed in claim 15, wherein said pin body section contains an additive composed of at least one of hydroxyapatite, calcium phosphate, calcium hydrogenphosphate, calcium carbonate, and calcium hydrogencarbonate.

* * * * *